(12) United States Patent
Goto et al.

(10) Patent No.: US 7,945,013 B2
(45) Date of Patent: May 17, 2011

(54) X-RAY CT APPARATUS

(75) Inventors: Taiga Goto, Tokyo (JP); Koichi Hirokawa, Tokyo (JP); Toshiyuki Irie, Ibaraki (JP)

(73) Assignee: Hitachi Medical Corporation, Tokyo (JP)

( * ) Notice: Subject to any disclaimer, the term of this patent is extended or adjusted under 35 U.S.C. 154(b) by 82 days.

(21) Appl. No.: 12/527,009

(22) PCT Filed: Feb. 14, 2008

(86) PCT No.: PCT/JP2008/052431
§ 371 (c)(1),
(2), (4) Date: Aug. 13, 2009

(87) PCT Pub. No.: WO2008/099877
PCT Pub. Date: Aug. 21, 2008

(65) Prior Publication Data
US 2010/0014630 A1    Jan. 21, 2010

(30) Foreign Application Priority Data
Feb. 14, 2007  (JP) .................................. 2007-033798

(51) Int. Cl.
*A61B 6/00*    (2006.01)
(52) U.S. Cl. ............................................ 378/16; 378/4

(58) Field of Classification Search ................. 378/4–20
See application file for complete search history.

(56) References Cited

U.S. PATENT DOCUMENTS
6,490,337 B1  12/2002  Nagaoka et al.
7,103,139 B2   9/2006  Nagaoka et al.

FOREIGN PATENT DOCUMENTS
JP   2001-276040   10/2001
JP   2002-263097    9/2002
JP   2006-116137    5/2006

*Primary Examiner* — Courtney Thomas
(74) *Attorney, Agent, or Firm* — Cooper & Dunham LLP

(57) ABSTRACT

An X-ray CT apparatus acquires a scanogram of an object to be examined, generates an ellipse model having an X-ray attenuation coefficient equivalent to that of water and approximated to a tomographic image of the obtained imaged portion from the feature quantity of the projection value profile, determines whether or not the generated elliptic model is adequate as a model of the imaged portion from another feature quantity with respect to the projection value profile, generates a corrected elliptic model according to yet another feature quantity with respect to the projection value profile if the elliptic model is determined to be inadequate, and controls the modulation of the tube current in an X-ray source so that a predetermined target SD value is maintained in any scanning position when a tomographic image is reconstructed according to X-rays transmitted through the object by using the elliptic model or the corrected elliptic model.

6 Claims, 8 Drawing Sheets

FIG.1
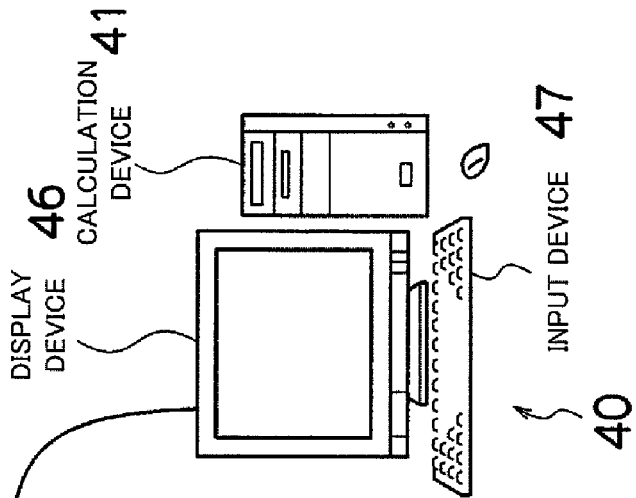
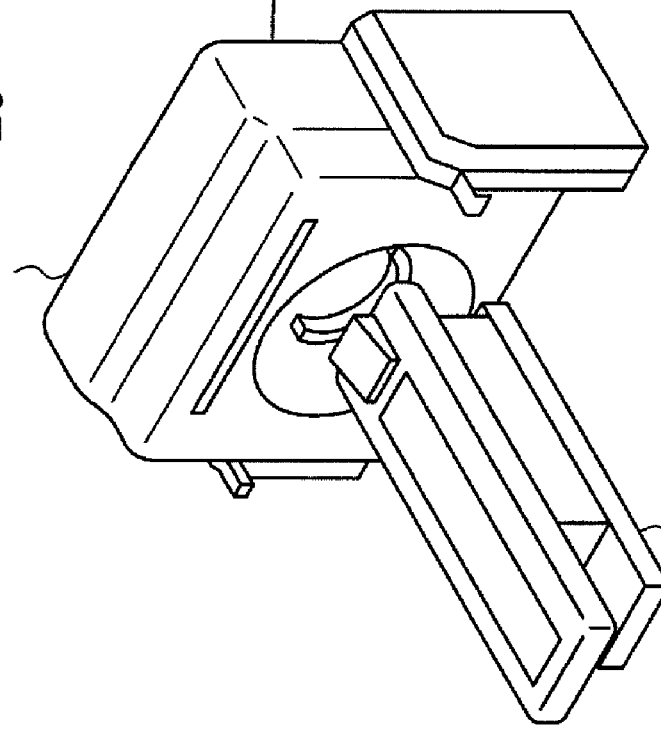

FIG.5
(a)
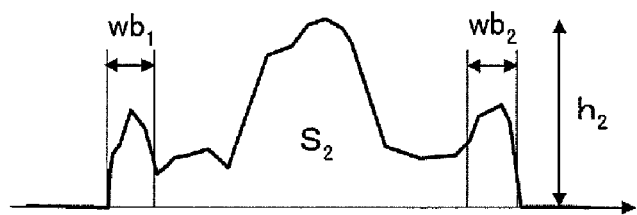
$A_2 = f(h_2)$
$B_2 = f(A_2, S_2)$
(b)
WATER-EQUIVALENT ELLIPTIC MODEL
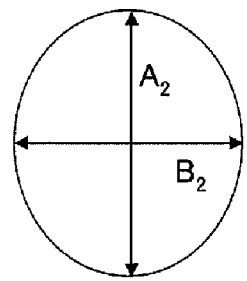
ATTENUATION COEFFICIENT
$\mu$
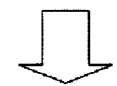
(c)
ATTENUATION COEFFICIENT
CORRECTED ELLIPTIC MODEL
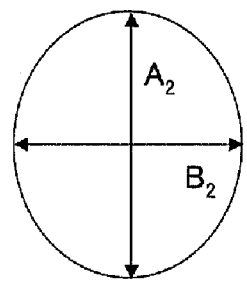
ATTENUATION COEFFICIENT
$\mu'$ FIG.6
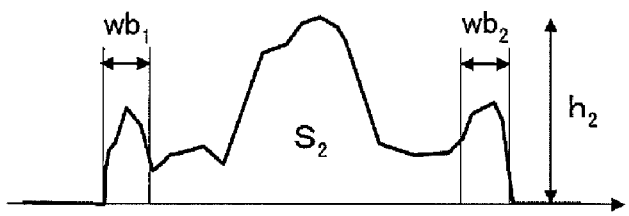
(a)
$A_2 = f(h_2)$
$B_2 = f(A_2, S_2)$
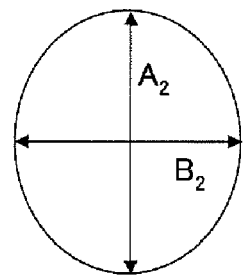
(b) WATER-EQUIVALENT ELLIPTIC MODEL
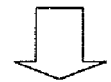
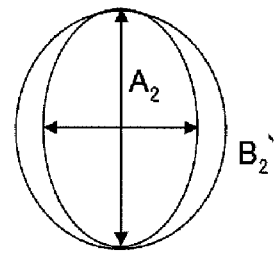
(c) SHAPE-CORRECTED ELLIPTIC MODEL FIG.8
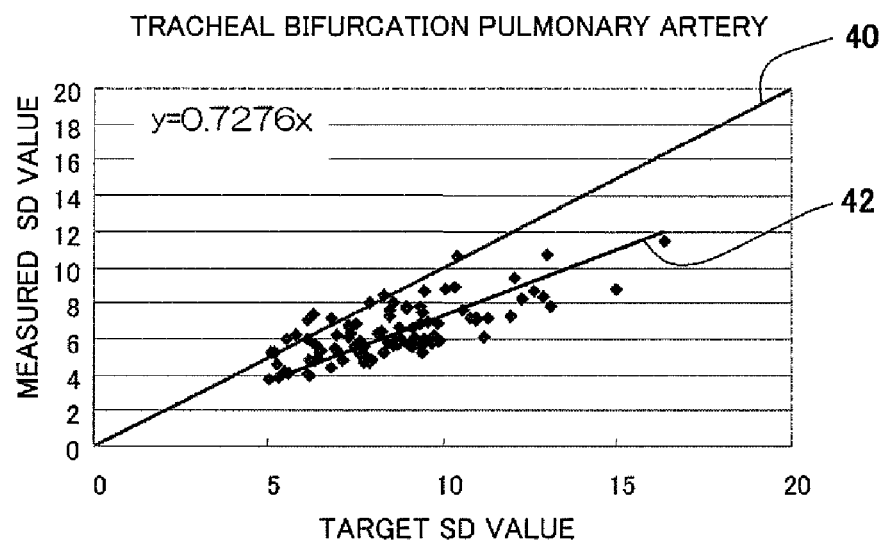
(a)
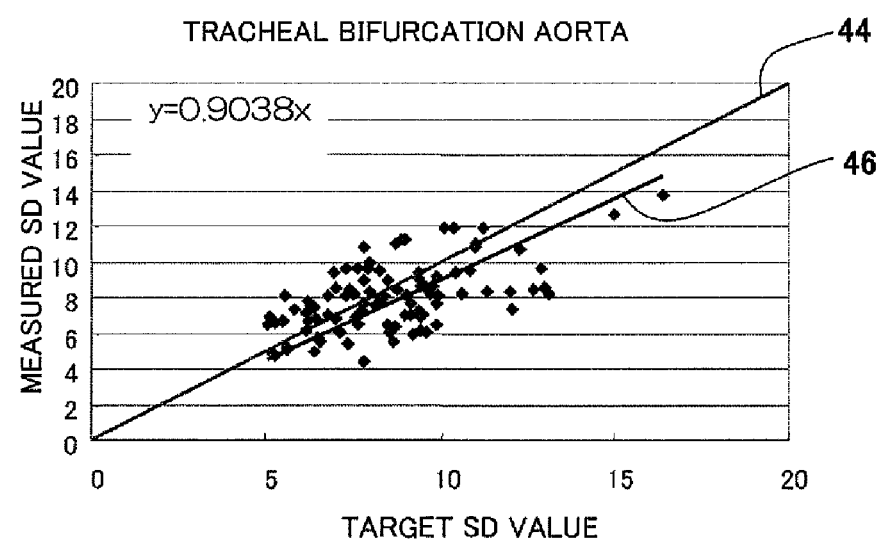
(b)

X-RAY CT APPARATUS

TECHNICAL FIELD

The present invention relates to upgrading of an X-ray CT apparatus that controls the modulation of X-ray dose to be irradiated to an object to be examined by using an elliptic model which is approximated to a human body, in order to achieve the target SD (Standard Deviation) in an image with respect to the image data of the object.

BACKGROUND ART

As for the method for evaluating noise (photon noise) of an X-ray CT apparatus, SD in an image has been used. The SD in an image indicates dispersion degree from the average value of pixel values, and the higher the noise is the greater the SD value becomes. Particularly, in the case of observing (diagnosing) a region in the object wherein the difference in CT values are small, i.e. CT values are comparatively homogeneous, it is necessary to reduce noise, i.e. to suppress SD value of the image.

One of the methods for reducing noise is to increase the number of photons (volume of information). It is known that the number of photons to be irradiated per unit time increases approximately in proportion to the square of tube voltage. Given this factor, tube voltage is increased in order to reduce noise, but since the number of photons increase by doing so, radiation exposure to the object also increases. Therefore, it is important to reduce radiation exposure to the object as much as possible, and perform scanning of the object with minimum radiation exposure necessary for diagnosis.

Also, attenuation ratio of X-rays at the time of transmitting to the object (ratio of X-ray irradiation with respect to the transmitted X-ray) is determined by the product of X-ray attenuation coefficient and transmitting distance. Therefore, the greater the X-ray attenuation coefficient of the object is and the longer the transmitting distance is due to the size of the object the greater the attenuation ratio becomes, which leads to the reduction of the number of photons and increase of noise.

Since the shape of cross-sections of an object is close to an ellipse, in the case of scanning the object using an X-ray CT apparatus by setting a constant tube current without depending on a revolving position (view angle), the number of photons after transmitting through the object varies by each view angle, thus the amount of noise also varies for each view angle. Since a CT image is acquired by reconstructing projection data at various view angles, image quality of the CT image is strongly influenced by projection data at the view angle having the most noise. In other words, even projection data of a certain angle has a small amount of noise, if the projection data of another angle has much noise, the CT image will have much noise, i.e. a high image SD value. For this reason, the technique for stabilizing noise for each revolving position by modulating tube current during revolution has been used in recent years.

In JP-A-2001-276040, the X-ray CT apparatus is disclosed which generates an elliptic model by presuming the shape of cross-sections of an object as an ellipse based on the projection value profile acquired by scanogram projection and controls the X-ray dose to be irradiated to the object with respect to every view angle using the generated model. In accordance with this X-ray CT apparatus, since the number of photons after being transmitted through the object can be stabilized regardless of the view angle if the generated elliptic model is adequate, it is possible to acquire CT images having the target image SD value while suppressing unnecessary radiation exposure.

DISCLOSURE OF THE INVENTION

However, in the X-ray CT apparatus disclosed in JP-A-2001-276040, though the target SD value in an image matches well with the actually measured SD value in the case of scanning the region having comparatively homogeneous X-ray attenuation coefficient such as abdominal region, there are cases that a great error can be caused between the target SD in an image and the actually measured SD value when scanning the region having inhomogenous X-ray attenuation coefficient such as a chest region.

The objective of the present invention is to solve the above-mentioned problem by providing an X-ray CT apparatus which has a function to control the modulation of X-ray irradiation dose using an elliptic model, capable of achieving a target image SD value while suppressing unnecessary X-ray radiation exposure to an object to be examined regardless of the scanning region and the revolving position thereof of the object.

The X-ray CT device of the present invention which achieves the above-mentioned objective comprises:
an X-ray source configured to irradiate X-rays to an object to be examined;
an X-ray detector disposed facing the X-ray source, configured to detect the X-rays transmitted through the object;
a scanner mounting the X-ray source and the X-ray detector, configured to rotate them around the object;
an image reconstruction device configured to reconstruct a tomographic image of the object based on the transmitted X-ray dose in a plurality of directions detected by the X-ray detector; and
an image display device configured to display the tomographic image,
characterized in further comprising:
an elliptic model generating function configured to generate an elliptic model including a circle, which is approximated to a cross-section of an scanning region of the object and has an X-ray attenuation coefficient effectively equivalent to that of water, based on the maximum height and the area of the projection value profile of the scanning region obtained by performing scanogram projection on the object;
an elliptic model adequacy determining function that determines whether the elliptic model is adequate as a model for the scanning region or not;
a corrected elliptic model generating function that generates the corrected elliptic model based on the amount of characteristic of the projection value profile in the case that the elliptic model adequacy determining function determined that the elliptic model is inadequate as the model for the imaging region; and
a radiation dose controlling function that controls the X-ray dose to be irradiated from the X-ray source based on the elliptic model or the corrected elliptic model.

In accordance with the present invention, since the modulation of the tube current of the X-ray tube mounted in the scanner is controlled for each revolving position of the scanner using an appropriate elliptic model respectively regardless of the scanning region of the object in which the X-ray attenuation coefficient is homogeneous or inhomogeneous, SD value of the tomographic image reconstructed based on the X-rays transmitted through the object is constantly maintained in the set target SD value, and radiation exposure to the object is maintained in the minimum level necessary for reaching the target SD value.

BRIEF DESCRIPTION OF THE DIAGRAMS

FIG. 1 is an external view of the X-ray CT apparatus to which the present invention is applied.

FIG. 5 shows a procedure for generating a corrected elliptic model to be implemented in S7 of FIG. 3.

FIG. 6 shows another procedure for generating a corrected elliptic model to be implemented in S7 of FIG. 3.

Figure 2:
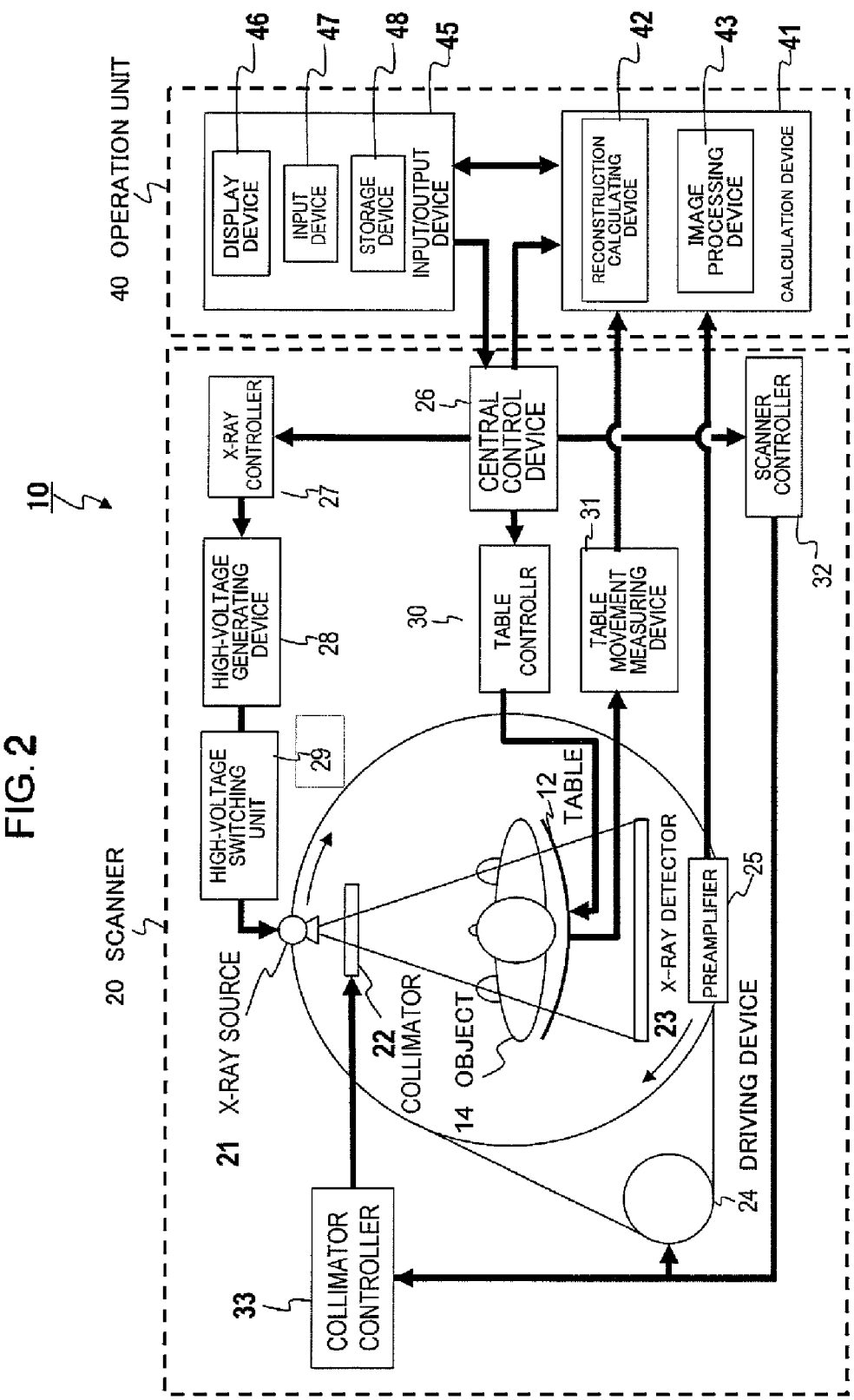
FIG. 2 is a block configuration diagram of the X-ray CT apparatus shown in FIG. 1.

FIG. 8 is for explaining the deviance between the relationship between the estimated target SD value and the actually measured SD value and the relationship between the actually measured target SD value and the actually measured SD value, with respect to the reconstructed tomographic image acquired by modulating the tube current on an imaging region having low homogeneity in the X-ray attenuation coefficient for each revolving position by applying an elliptic model having the X-ray attenuation coefficient which is equivalent to that of water.

BEST MODE FOR CARRYING OUT THE INVENTION

The best mode for carrying out the present invention will be described below based on the attached diagrams.

The configuration of the X-ray CT apparatus to which the present invention is applied will be described referring to FIG. 1 and FIG. 2.

As shown in FIG. 1, an X-ray CT apparatus 10 is mainly configured by:
a table 12 for moving an object to be examined;
a scanner 20 for scanning the object;
a calculation device 41 for processing the data acquired from the X-ray detector provided in the scanner 20 and reconstructing a tomographic image;
a display device 46 for displaying the reconstructed tomographic image; and
an input device 47 configured by devices such as a mouse and a keyboard, for inputting measurement/reconstruction parameters such as table moving velocity information or reconstruction positions.

The block configuration of the X-ray CT apparatus 10 whose external view is shown in FIG. 1 is shown in FIG. 2. This X-ray CT apparatus 10 is configured by:
a scanner 20 wherein the X-ray source 21 for irradiating X-rays in a fan-like form and the X-ray detector 23 which is disposed facing the X-ray source and has a number of (about 1000) X-ray detection elements, are disposed on a circular rotating disc centering on the center of the object for scanning an object 14, using the rotate-rotate system (third generation) that collects attenuation data of the X-rays irradiated to the object by rotating the circular rotating disc;

a table 12 mainly for placing and moving the object 14; and
an operation unit 40 for inputting scanning condition or operating reconstruction, display, etc. of tomographic images.

The scanner 20 is mainly configured by:
an X-ray source 21 for irradiating X-rays;
a collimator 22 for adjusting X-ray irradiation angle, etc. from the X-ray source 21;
a driving device 24 for rotating the devices such as X-ray source 21 and the X-ray detector 23 on the circular rotating disc;
a central control device 26 for controlling the respective units in the scanner 20;
an X-ray controller 27 for controlling the generation of X-rays;
a high-voltage generating device 28 for applying a voltage to the X-ray source 21;
a high-voltage switching unit 29 for controlling a high voltage generated in the high-voltage generating device 28;
a table controller 30 for controlling the operation of the table 12;
a table movement measuring device 31 for measuring moving velocity of the table 12, etc.;
a scanner controller 32 for controlling the operation of the scanner; and
a collimator controller 33 for controlling the collimator 22.

The operation unit 40 is mainly configured by a calculation device 41 and an input/output device 45. The calculation unit 41 is mainly configured by:
a reconstruction calculation device 42 to which the X-ray attenuation data detected by the X-ray detector 23 is inputted, for processing the attenuation data (projection data) thereof and reconstructing a tomographic image; and
an image processing device 43 for processing the reconstructed tomographic image. The input/output device 45 is configured by:
a display device 46 for displaying the reconstructed tomographic image; and
an input device 47 for inputting information such as scanning condition; and
a storage device 48 for storing the reconstructed tomographic image.

The X-ray CT apparatus configured as above is to be operated as below.

When an operator inputs scanning condition (tube current, tube voltage, revolving velocity of a circular rotating disc and helical pitch) and reconstruction condition (image FOV, reconstruction filter, image slice thickness, reconstruction slice position, etc.) using the input device 47, control signals necessary for scanning are transmitted to the X-ray controller 27 based on the command, table controller 30 and scanner controller 32 from the central control device 26, and the scanning is started upon receiving an scanning start signal. When the scanning is started, control signals are transmitted from the X-ray controller 27 to the high-voltage generating device 28, high voltage is applied from the high-voltage generating device 28 to the X-ray source 21 via the high-voltage switching unit 29, and X-rays are irradiated from the X-ray source 21 to the object 14. On the other hand, control signals are transmitted from the scanner controller 32 to the driving device 24, and the X-ray 21, collimator 22, X-ray detector 23 and pre-amplifier 25 are rotated centering around the object 14. Also by the table controller 30 and the table movement velocity measuring device 31, the table 12 on which the object 14 is placed is remained stationary (upon circle-scanning) or moved in parallel in the rotation axis direction of the X-ray source 21, etc. (upon helical scanning). The irradiated X-rays are restricted in their irradiation region including an irradiation angle by the collimator 22 controlled by the collimator controller 33, absorbed (attenuated) in the respective tissues in the object 14, and the X-rays transmitted through the object 14 are detected by the X-ray detector 23.

The X-rays detected in the X-ray detector 23 are converted into electric signals, and inputted to the calculation device 41 as projection data. The projection data inputted to the calculation device 41 is processed with image reconstruction process by the reconstruction calculation device 42 in the calculation device 41. The reconstructed image is stored in the storage device 48 in the input/output device 45, and displayed on the display device 46 as a CT image. Or, after being processed in the image processing device 43, it can be displayed on the display device 46 as a CT image.

In the X-ray CT apparatus 10 of the present invention, for the purpose of reducing radiation dose, a tube current (applicable also to a tube voltage) to be applied to the X-ray source is modulated so as to control the radiation dose for each revolving position (view angle) during revolution of the devices such as X-ray source 21 and X-ray detector 23. This is for stabilizing noise for each view by controlling irradiation dose by modulating the tube current during scanning rotation and stabilizing the number of photons regardless of X-ray passing direction. Control of irradiation dose is carried out based on the set irradiation dose modulation curve (in the present invention, irradiation dose modulation function expressing the relationship between the revolution angle and the tube current). Therefore, it is necessary to use an adequate elliptic model in accordance with the scanning region of the object 14, respectively for the case of scanning the region having high homogeneity in X-ray attenuation coefficient and the case of scanning the region having low homogeneity in X-ray attenuation coefficient.

FIG. 8(*a*) and FIG. 8(*b*) show the examples of actually measured SD values of the image acquired under irradiation dose control, using the elliptic model which is not adequate for the scanning region.

Line 40 in FIG. 8(*a*) expresses the relationship Y=X between the estimated target SD value with respect to the elliptic model having an X-ray attenuation coefficient equivalent to that of water and the actually measured image SD value in the case that the scanning region is a tracheal bifurcation pulmonary artery, and line 42 indicates that the relationship between both sides in the actual measurement is Y=0.7276X.

Line 44 in FIG. 8(*b*) expresses the relationship Y=X between the estimated target SD value with respect to the elliptic model having the X-ray attenuation coefficient which is equivalent to that of water and the actually measured SD value in the case that the scanning region is a tracheal bifurcation aorta, and line 46 expresses that the relationship of both sides in the actual measurement is Y=0.9038X. In the case of scanning the region having low homogeneity in X-ray attenuation coefficient using the elliptic model having an X-ray attenuation coefficient equivalent to that of water, there is a tendency that the actually measured SD value is lower compared to the target SD value, i.e. the noise is reduced surpassing the target value.

Hereinafter, generation of the elliptic model according to the scanning region of the object 14 and the correction thereof, and generation of radiation dose (tube current) modulating function using the generated or corrected elliptic model related to the present invention will be described.

Figure 3:
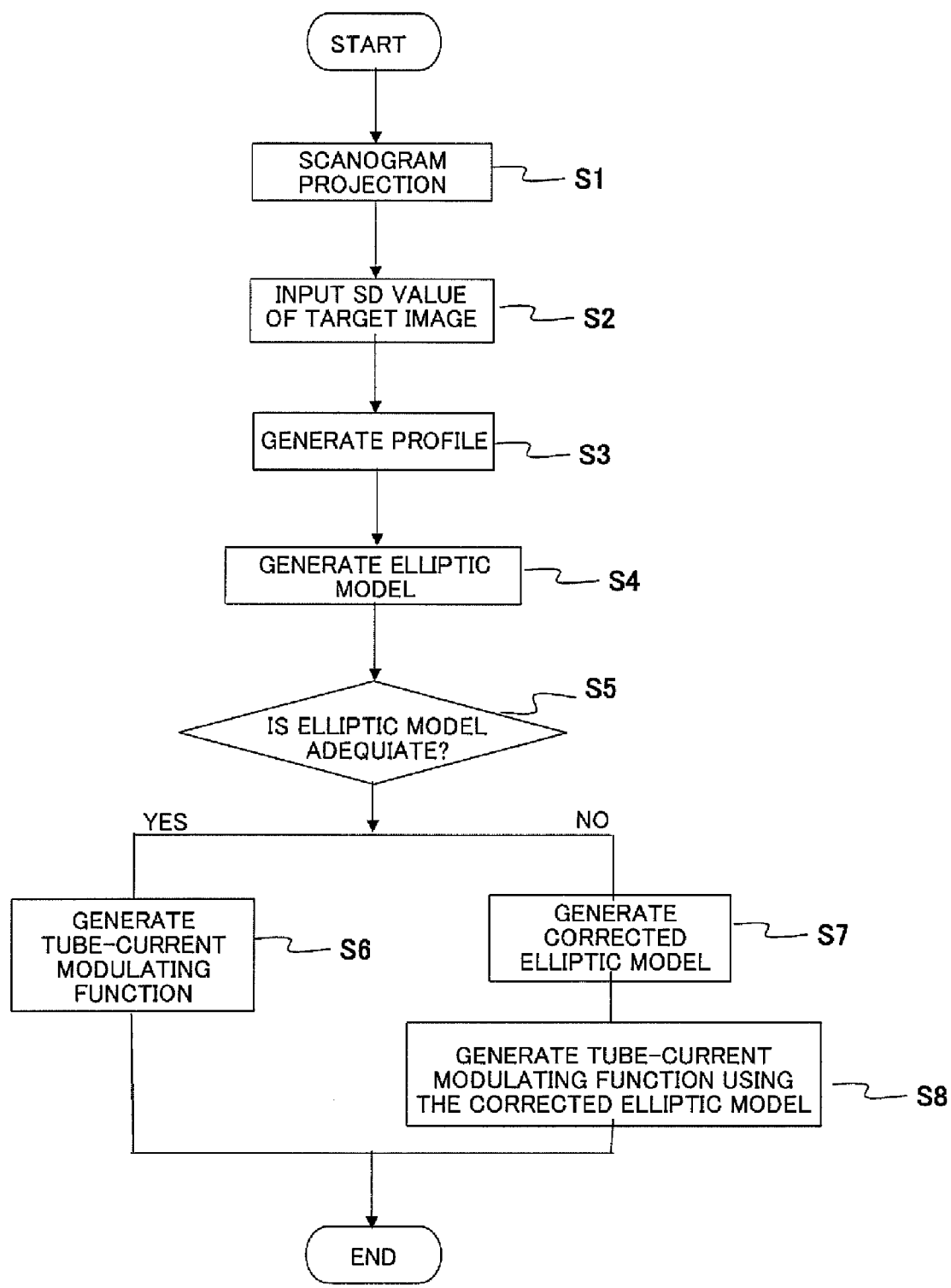
FIG. 3 is a flowchart showing the function of the X-ray CT apparatus shown in FIG. 2 to which the present invention is applied.
Figure 4:
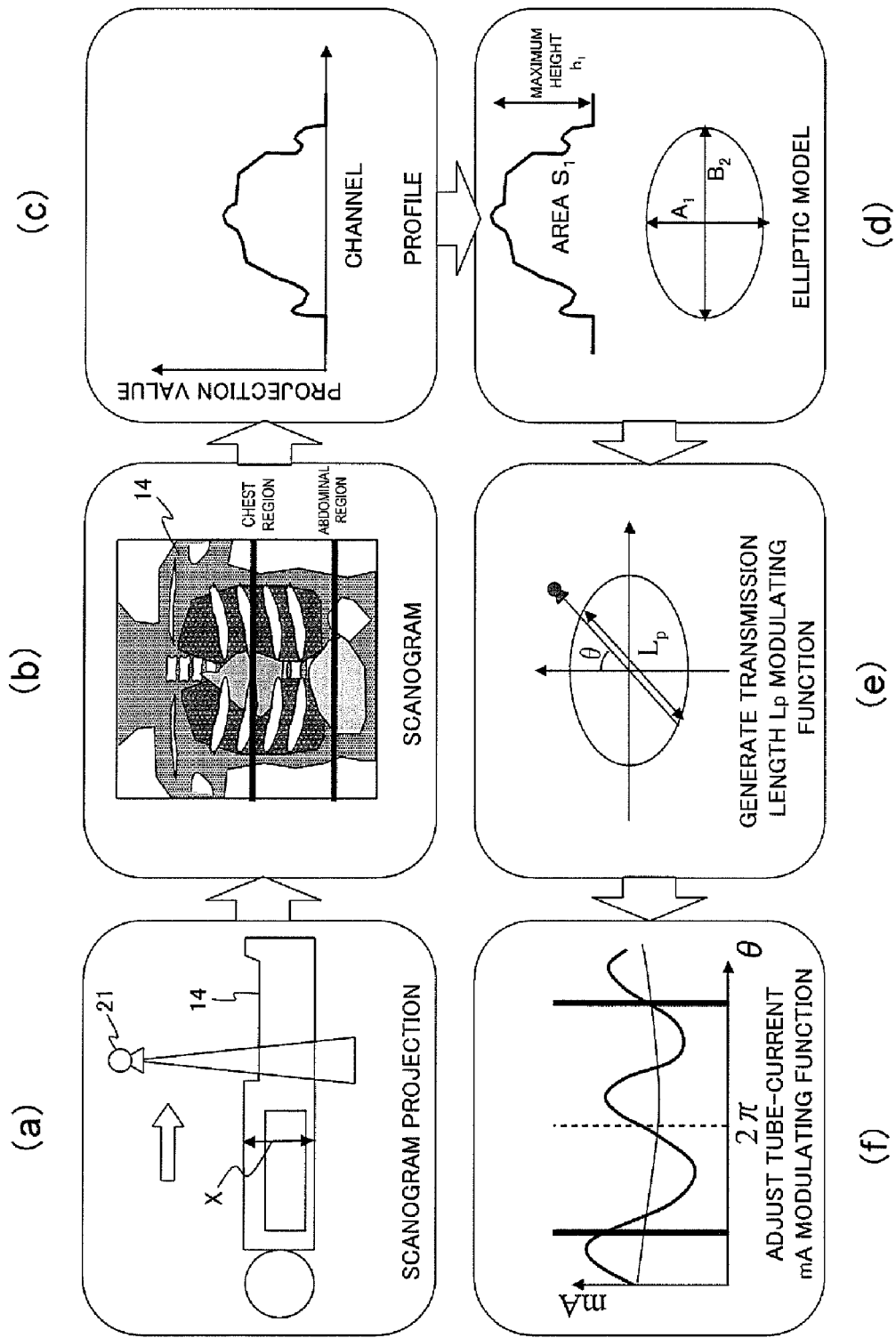
FIG. 4 is a view showing frame formats of each process in the flowchart shown in FIG. 3.

FIG. 3 is a flowchart explaining the function implemented in the present invention to be applied to the X-ray CT apparatus 10. FIG. 4 is a view showing a frame format of each process in the flowchart shown in FIG. 3. These functions to be explained in a flowchart form are stored in the storage device 48 in the form of, for example, a program, and various parameters therefore are inputted using the input device 47 on each use. First in step S1 of FIG. 3, scanogram projection is performed on an scanning region and the surrounding area of the object by holding the X-ray source 21 on the upper side of the object 14, for example, in the revolving position of view angle 0° as shown in FIG. 4(*a*), then moving the scanner 20 or the table 12 in the body-axis direction of the object 14 while irradiating X-rays therefrom, so as to acquire a scanogram as shown in FIG. 4(*b*). The scanning region of the object 14 is first determined using the acquired scanogram.

In step S2, with respect to the determined scanning region, the target SD value desired to be acquired by the scanning is inputted using the input device 47.

Next in step S3, distribution of projection values of, the determined scanning region as shown in FIG. 4(*c*), for example, projection value profile of an abdominal region, i.e. the case of setting the channel expanse of the X-ray detector 23 as the lateral axis and projection value (attenuation data) as the longitudinal axis, is generated from the projection data of the previously acquired scanogram.

Next in step S4, from the previously generated projection value profile of an abdominal region, assuming that the shape of the cross-section of the abdominal region is an ellipse, the elliptic model having the X-ray attenuation coefficient effectively equivalent to that of water is generated using the following procedure. An elliptic model in the case of assuming that the scanning region is an elliptic form is generated by obtaining projection value profile area S1 as the area of the elliptic model, by setting the longitudinal axis length of the elliptic model thereof as A1 and projection value maximum height as h1, and obtaining the lateral axis length B1 of the elliptic model by applying the values of A1 and h1 to the formula for calculating the area of an ellipse.

While lateral axis B1 is set as the major axis and longitudinal axis A1 is set as the minor axis in the elliptic model of FIG. 4(*d*), depending on the scanning condition in the case of scanning from the side of the object 14, there are cases that lateral axis B1 is set as the minor axis and longitudinal axis A1 is set as the major axis, or lateral axis B1 and longitudinal axis A1 are equal in length.

Next in step S5, determination on whether or not the previously generated elliptic model having the X-ray attenuation coefficient effectively equivalent to that of water is adequate for the elliptic model of the relevant scanning region is carried out by one of the following two methods.

<First Adequacy Determining Method>

First, the area of the projection profile actually acquired upon scanogram projection shown in FIG. 4(*a*) is calculated. Next, the area of the projection value profile acquired when X-rays are virtually irradiated to the elliptic model generated in step 4 from the same revolving position as that at the time when actual scanogram projection is calculated. Then the area difference between the two projection value profiles is calculated, and compared with a predetermined value. When the area of difference is larger than a predetermined value, for example, 50% of the area of the actually acquired projection value profile, it is determined that the elliptic model generated in step S4 is not adequate. In reverse case, it is determined that the elliptic model generated in step S4 is adequate as the elliptic model for the relevant scanning region of the object 14.

While 50% of the projection value area calculated from the profile of the projection value actually obtained as a predetermined difference area is set as a predetermined value in the present example, the predetermined value to be set does not have to be limited thereto.

<Second Adequacy Determining Method>

Whereas the projection value profile upon scanogram projection in the region wherein CT values are comparatively homogeneous such as an abdominal region shows one big mountain-shaped curve, the projection value profile upon scanogram projection in the region wherein CT values are not homogenous such as a chest region tends to have a curve having a plurality of mountains in the channel direction.

The present example determines whether the elliptic model generated in step S4 having an X-ray attenuation coefficient effectively equivalent to that of water is adequate or not as a model for the relevant scanning region of the object 14, focusing on the shape of the projection value profile.

More specifically, in the case that the projection value profile upon scanogram projection in the relevant scanning region of the object 14 has more than two big peaks, it is determined that the elliptic model is not adequate for an elliptic model in the relevant scanning region of the object 14. In the case that the projection value profile has one peak, it is determined that the elliptic model is adequate for the elliptic model in the relevant scanning region of the object 14.

When the elliptic model generated in step S4 is determined as adequate in step S5 (YES in step 5), a tube current modulating function is generated using the elliptic model (step S6). The method for generating a tube current modulating function will be described later in detail.

When the elliptic model generated in step S4 is determined as inadequate in step S5 (No in S5), a corrected elliptic model is to be generated (step S7). As examples for generating a corrected elliptic model, three methods will be described below.

<First Method for Generating a Corrected Elliptic Model>

This method, as shown in FIG. 5, is for correcting X-ray attenuation coefficient μ which is effectively equivalent to that of water to another X-ray attenuation coefficient μ' using the characteristic of the projection value profile shown in FIG. 5(a) without changing the shape of the elliptic model generated in step S4.

More specifically, components Wb1 and Wb2 that are equivalent to the body surface portion such as a bone which is different from a lung field region are extracted from the projection value profile in FIG. 5(a), and X-ray attenuation coefficient correction amount F1(Wb1+Wb2) is obtained as below based on the extracted components.

$$F1(Wb1+Wb2)=C1\times(Wb1+Wb2) \quad (1)$$

Here, C1 is an arbitrary constant number.

Using this X-ray attenuation coefficient correction amount F1(Wb1+Wb2), corrected X-ray attenuation coefficient μ' is to be obtained as below.

$$\mu'=\mu-F1(Wb1+Wb2)=\mu-C1\times(Wb1+Wb2) \quad (2)$$

In this manner, generation of the elliptic model of which the X-ray attenuation coefficient is corrected is performed.

The value of C1 is determined based on the result of the actual measurement as shown in FIG. 8.

<Second Method for Generating a Corrected Elliptic Model>

As shown in FIG. 6, this method, with respect to the elliptic model generated in step 4, is for correcting axis-length B2 in the width direction of the object to axis length B2' in the width direction using characteristic of the projection value profile shown in FIG. 6(a) without changing the axis length in the thickness direction of the object. More specifically, components Wb1 and Wb2 that are equivalent to the body-surface portion such as a bone different from the lung field region are extracted from the projection value profile in FIG. 6(a), and width-direction axis-length corrected amount F2 (Wb1+Wb2) is to be obtained as below based on the extracted components.

$$F2(Wb1+Wb2)=C2\times(Wb1+Wb2) \quad (3)$$

Here, C2 is an arbitrary constant number.

Corrected width-direction axis-length B2' is to be obtained using this width-direction axis-length corrected amount F2(Wb1+Wb2).

$$B2'=B2-F2(Wb1+Wb2)=B2-C2\times(Wb1+Wb2) \quad (4)$$

In this manner, a shape-corrected elliptic model is generated.

The value of C2 is determined based on the result of the actual measurement as shown in FIG. 8.

<Third Method for Generating a Corrected Elliptic Model>

Figure 7:
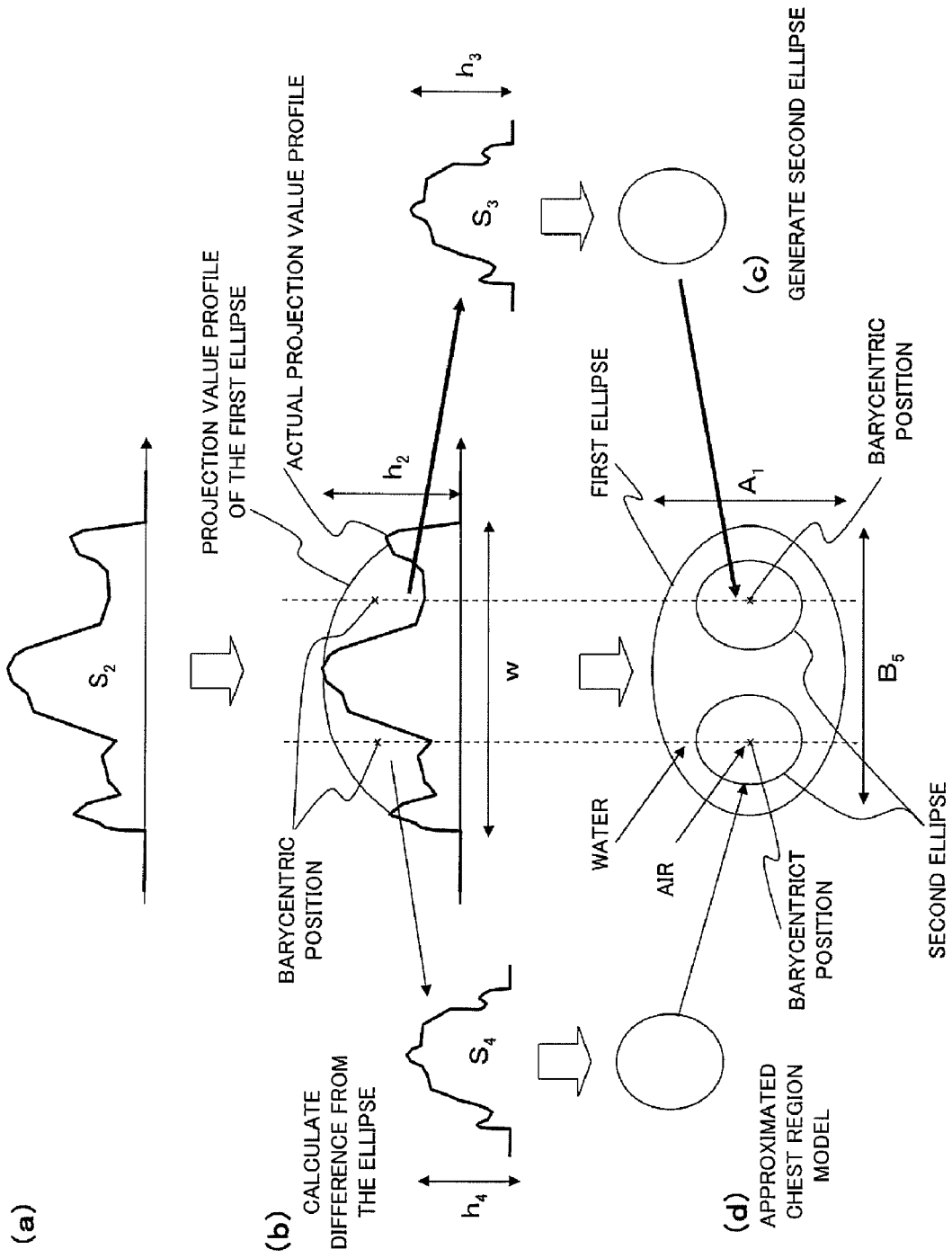
FIG. 7 shows yet another procedure for generating a corrected elliptic model to be implemented in S7 of FIG. 3.

This method, as shown in FIG. 7, is for generating a corrected elliptic model, after generating a first ellipse having X-ray attenuation coefficient "μ" which is effectively equivalent to that of water based on the profile generated in step S3, by inserting a second ellipse having X-ray attenuation coefficient "μa" which is effectively equivalent to that of air into the inside of the first ellipse.

First, a procedure for generating the first ellipse having X-ray attenuation coefficient "μ" which is effectively equivalent to that of water will be described.

The first ellipse is generated, by obtaining projection value maximum height h2 and channel-direction width "w" from the actual projection value profile shown in FIG. 7, setting projection value maximum height h2 as axis-length A1 in the thickness-direction of the first ellipse, and setting axis-length B5 in the width-direction of the first ellipse as width "w" in the channel-direction of the object.

Next, the procedure for generating the second ellipse to be inserted into the inside of the first ellipse, having X-ray attenuation coefficient "μa" which is effectively equivalent to that of air will be described.

By simulating scanogram projection of the first ellipse, the simulated profile of the projection value is generated. With respect to every two regions encompassed by the inside of simulated profile of the projection value of the first ellipse and the outside of the profile of the actual projection value, projection value area of the difference between the simulated profile of the projection value of the first ellipse and the profile of the actual projection value (difference profile) (shaded part in FIG. 7(b)) is calculated. These projection value areas S3 and S4 of the calculated difference profile correspond to the area of the respective second ellipses.

With respect to every region encompassed by the simulated profile of the projection value of the first ellipse and the profile of the actual projection value, second ellipses are generated for the same number as that of the regions thereof. As shown in FIG. 7(c), projection value maximum heights h3,h4 and projection value areas S3,S4 of the respective difference profiles are obtained, and the second ellipses are generated based on the result thereof. Here, the axis length in the thickness direction of the object in the second ellipse is calculated from the projection value maximum heights h3,h4 of the difference profile, and the axis length in the width direction of the object in the second ellipse is calculated by applying the projection value difference maximum heights h3,h4 and projection value areas S3,S4 of the difference profile to the formula for calculating the area of an ellipse.

Then by inserting the obtained second ellipse into the inside of the first ellipse, the corrected ellipse model is generated. The position in the width direction of the object into which the second ellipse is inserted is set by the barycentric position of the region of the difference profile (shaded part in FIG. 7(b)). In other words, it is the position that the barycentric position of the second ellipse to be inserted into the first ellipse matches the barycentric position of the region of the difference profile by which the second ellipse is generated (refer to FIG. 7(b), (d)). Also, the position in the thickness direction of the object into which the second ellipse is inserted is the position wherein the level of the barycentric position of the second ellipse which is inserted into the first ellipse matches the barycentric position of the first ellipse, i.e. the center of the object in the first ellipse in the thickness direction (A1/2).

In this manner, the corrected ellipse model having two second ellipses having the X-ray attenuation coefficient which is effectively equivalent to that of air inside of the first ellipse having the X-ray attenuation coefficient which is effectively equivalent to that of water is generated.

Next in step S8, a tube current modulating function is generated using the corrected elliptic model generated in step S7. The method for generating a tube current modulating function will be described later in detail.

Hereinafter, generation of a tube current modulating function using the elliptic model or corrected elliptic model to be carried out in step S6 and step S8 will be described in detail.

As shown in FIG. 4(d) and (e), transmission distance $Lp(\theta)$ of the X-ray beams to be irradiated from revolving position $\theta$ and pass through the center of the elliptic model or the corrected elliptic model is calculated based on the formula below.

$$Lp(\theta) = A \times B / (A^2 \times \cos^2\theta + B^2 \times \sin^2\theta)^{0.5} \quad (5)$$

Here, A and B are the length of the longitudinal axis and the lateral axis of the elliptic model or the corrected elliptic model.

Based on the obtained transmission distance $Lp(\theta)$, the modulation of irradiation dose $mAs(\theta)$ for each revolving position is controlled so that the noise (variance value $\sigma^2$) corresponding to the target SD value expressed by formula 6 becomes uniform.

$$\sigma^2 = \sigma base^2 \times CST \times CmAs \times CL \times CRW \times CRF \quad (6)$$

Here, CST (slice thickness), CmAs (irradiation dose (tube current×revolving velocity)), CL (transmission distance), CRW (reconstruction view weight) and CRF (reconstruction filter) are terms for considering the influence exerted by the respective differences on the reference value, and can be obtained as below.

$CST = STbase/ST$ $CmAs = \Sigma\{mAsbase/mAs(\theta)\}$ $CL = \Sigma \exp(\mu p(Lp(\theta) - Lbase))$ $CRW = \Sigma\{W(\theta)^2\}/\{\Sigma W(\theta)\}^2$ $CRF = \sigma RF^2 / \sigma RF_{base}^2 \quad (7)$ Lbase, mAsbase and STbase are the diameter of the circular model wherein the reference cross-section of the object measured in advance for each tube voltage is simulated as a circular form, irradiation amount (tube voltage×revolving velocity) and slice thickness, $W(\theta)$ is a reconstruction view weight, $\theta$ is a view angle (revolving position), $\sigma base^2$ is a noise (variance value) acquired from the image obtained by performing reconstruction for 360 degrees on the projection data which is scanned by the condition of Lbase, mAsbase and ST base without performing view weighting. Also, CRW is 1 when reconstruction view weighting is not performed, and it becomes greater by performing reconstruction view weighting. Also, though concrete explanation will be omitted here, reconstruction view weighting is associated also with helical pitch, and CRF becomes greater when helical pitch is great due to decrease of the data volume which is usable for reconstruction. As for the CRF, commonly used reconstruction filter for an abdominal region is used as a reference, and the value of CRF is 1 in the case of using the reconstruction filter, and the value of CRF becomes greater than 1 in the case of using the filter whose high-frequency is enhanced.

In the case of scanning a plurality of regions at once using helical scan when it is necessary to change noise level in accordance with the region, the target irradiation dose (tube current×revolving velocity) mAs ($\theta$) can be achieved by setting a plurality of lines (for each region) to determine noise (the region where a target tissue exists) and changing $\sigma base^2$ and Lbase in the set lines.

As for the method for controlling irradiation dose based on the noise amount, it does not have to be limited to the above-described method and any common method may be used.

By controlling irradiation dose (tube current×revolving velocity) based on the set radiation dose modulating function (refer to FIG. 4(f)) to perform scanning, it is possible to stabilize the number of photons of the X-rays which are transmitted through the object in any region of the object 14 regardless of X-ray passing direction, which leads to stabilization of the noise for each view.

In accordance with the above-described embodiment of the present invention, it is possible to modulate a tube current by determining whether an scanning region has high homogeneity or low homogeneity in X-ray attenuation coefficient based on the projection value distribution (profile) in the scanogram and correcting an elliptic model according to the scanning region. As a result, it is possible to stabilize the dose of X-rays which transmit through the object regardless of revolving position of X-rays, and to obtain the reconstructed image having appropriate SD value constantly without depending on the scanning region. Also, radiation exposure to the object can be reduced by suppressing unnecessary radiation dose.

Also, in accordance with the above-described embodiment of the present invention, it is possible to automatically and easily determine whether the scanning region has high homogeneity or low homogeneity in X-ray attenuation coefficient. Therefore, the elliptic model which is adequate for the scanning region, i.e. the elliptic model to be applied to the region having high homogeneity in X-ray attenuation coefficient and the corrected elliptic model to be applied to the region having low homogeneity in X-ray attenuation coefficient can be generated in accordance with actual condition of the scanning region. Accordingly, the X-ray dose to be transmitted through the object can be stabilized without depending on the revolving position of the object to be scanned.

Also, while a commonly used X-ray CT apparatus having one set of an X-ray source and an X-ray detector is described in the above-described embodiment of the present invention, the present invention is applicable also to the multi-source X-ray CT apparatus having plural sets of the X-ray source and the X-ray detector.

Also, while scanogram projection is performed from the upper side of the object in the above-described embodiment of the present invention, the scanogram projection may be performed from the side of the object. In this case, the number of second ellipse in the third corrected elliptic model is one.

The invention claimed is:

1. An X-ray CT apparatus comprising:
    an X-ray source configured to irradiate X-rays to an object to be examined;
    an X-ray detector disposed facing the X-ray source, configured to detect the X-rays which are transmitted through the object;
    a scanner in which the X-ray source and the X-ray detector are mounted, configured to rotate them around the object;
    an image reconstruction device configured to reconstruct a tomographic image in an imaging region of the object based on the transmitted X-ray dose from a plurality of directions detected by the X-ray detector; and
    an image display device configured to display the reconstructed tomographic image,
    characterized in further comprising:
    an elliptic model generating function configured to generate an elliptic model including a circle, which is approximated to the cross section of an imaging region of the object and has an X-ray attenuation coefficient which is effectively equivalent to that of water, based on the maximum height and the area of the projection value profile of the imaging region of the object which is acquired by scanogram imaging;
    an elliptic model adequacy determining function configured to determine whether an elliptic model is adequate for the model of an imaging region or not;
    a corrected elliptic model generating function configured to generate a corrected elliptic model based on the amount of characteristic of the projection value profile in the case that the elliptic model is determined to be inadequate for the model of the imaging region by the elliptic model adequacy determining function; and
    a radiation dose controlling function configured to control the X-ray dose to be irradiated from the X-ray source based on the elliptic model or the corrected elliptic model.

2. The X-ray CT apparatus according to claim 1, wherein the elliptic model adequacy determining function determines whether the elliptic model is adequate or not, based on the difference between the area of the projection value profile acquired by virtually-performing a scanogram projection on the elliptic model from the same revolving position as that at the time when the scanogram projection is performed on the object and the area of the projection value profile of the imaging region.

3. The X-ray CT apparatus according to claim 1, wherein the elliptic model adequacy determining function determines whether the elliptic model is adequate or not based on the number of peaks in the projection value profile of the imaging region.

4. The X-ray CT apparatus according to claim 1, wherein the corrected elliptic model generating function corrects X-ray attenuation coefficient of the elliptic model based on the amount of characteristic of the projection value profile in the imaging region.

5. The X-ray CT apparatus according to claim 1, wherein the corrected elliptic model generating function corrects the axis-length equivalent to the length of the elliptic model in the width-direction of the object based on the amount of characteristic of the projection value profile in the imaging region.

6. The X-ray CT apparatus according to claim 1, wherein the corrected elliptic model generating function generates the corrected elliptic model by generating a first elliptic model having an X-ray attenuation coefficient effectively equivalent to that of water based on the amount of characteristic of the projection value profile of the imaging region, generating one or more second elliptic models having an X-ray attenuation coefficient effectively equivalent to that of air from the amount of characteristic the projection value profile generated based on the difference between the projection value profile acquired by virtually-performing a scanogram projection on the first elliptic model from the same revolving position as that at the time when the scanogram projection is performed on the object and the projection value profile of the imaging region, and inserting the second elliptic model(s) into the first elliptic model.

* * * * *